(12) United States Patent
Walker

(10) Patent No.: US 9,913,876 B2
(45) Date of Patent: *Mar. 13, 2018

(54) BIOGEL

(71) Applicant: Haemostatix Limited, Nottingham (GB)

(72) Inventor: Greg Walker, Nottingham (GB)

(73) Assignee: Haemostatix Limited, Nottingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/098,028

(22) Filed: Apr. 13, 2016

(65) Prior Publication Data

US 2016/0287659 A1   Oct. 6, 2016

Related U.S. Application Data

(63) Continuation of application No. 12/515,721, filed as application No. PCT/GB2007/004538 on Nov. 27, 2007, now Pat. No. 9,339,584.

(30) Foreign Application Priority Data

Nov. 27, 2006 (GB) .................... 0623607.9

(51) Int. Cl.
| | | |
|---|---|---|
| A61K 38/07 | (2006.01) |
| A61L 24/06 | (2006.01) |
| A61L 24/10 | (2006.01) |
| A61K 9/00 | (2006.01) |
| A61L 24/00 | (2006.01) |

(52) U.S. Cl.
CPC ............ A61K 38/07 (2013.01); A61K 9/0014 (2013.01); A61L 24/0015 (2013.01); A61L 24/0031 (2013.01); A61L 24/06 (2013.01); A61L 24/10 (2013.01); A61L 24/106 (2013.01); A61L 2400/04 (2013.01)

(58) Field of Classification Search
None
See application file for complete search history.

(56) References Cited

U.S. PATENT DOCUMENTS

| | | | |
|---|---|---|---|
| 4,377,572 | A | 3/1983 | Schwarz et al. |
| 4,427,651 | A | 1/1984 | Stroetmann |
| 5,357,042 | A | 10/1994 | Matsueda et al. |
| 5,635,477 | A | 6/1997 | Degrado et al. |
| 6,083,902 | A | 7/2000 | Cederhom-Williams |
| 6,113,948 | A | 9/2000 | Heath et al. |
| 6,391,343 | B1 | 5/2002 | Yen |
| 7,129,210 | B2 | 10/2006 | Lowinger et al. |
| 2002/0037323 | A1 | 3/2002 | Prasch et al. |
| 2003/0212253 | A1 | 11/2003 | Hammond et al. |
| 2005/0069589 | A1 | 3/2005 | Lowinger et al. |
| 2005/0123588 | A1 | 6/2005 | Zhu et al. |
| 2006/0089587 | A1 | 4/2006 | Nakatani et al. |
| 2006/0104970 | A1 | 5/2006 | Margel et al. |
| 2006/0110381 | A1 | 5/2006 | Pendharkar et al. |
| 2006/0204490 | A1 | 9/2006 | Pendharkar et al. |
| 2008/0051562 | A1 | 2/2008 | Chaikof et al. |
| 2008/0064628 | A1 | 3/2008 | Goodall et al. |

FOREIGN PATENT DOCUMENTS

| | | |
|---|---|---|
| CN | 1544098 A | 11/2004 |
| CN | 1863560 A | 11/2006 |
| EP | 0 831 793 A1 | 4/1998 |
| EP | 1329438 A1 | 7/2003 |
| EP | 1621220 A1 | 2/2006 |
| GB | 2429153 A | 2/2007 |
| IN | 2008/01191 P1 | 6/2008 |
| NZ | 523425 A | 2/2006 |
| RU | 2 096 415 C1 | 11/1997 |
| WO | 93/07170 A1 | 4/1993 |
| WO | 94/22910 A1 | 10/1994 |
| WO | 96/18388 A2 | 6/1996 |
| WO | WO 96/17633 * | 6/1996 |
| WO | 96/39128 A1 | 12/1996 |
| WO | 98/17319 A2 | 4/1998 |
| WO | 99/25383 A1 | 5/1999 |
| WO | 01/97872 A1 | 12/2001 |
| WO | 2002/058750 A2 | 8/2002 |
| WO | 2003/086494 A1 | 10/2003 |
| WO | 2004/098680 A1 | 11/2004 |
| WO | 2005/035002 A1 | 4/2005 |
| WO | 2005/076827 A2 | 8/2005 |
| WO | 2006/012541 A2 | 2/2006 |
| WO | 2006/044882 A2 | 4/2006 |
| WO | 2007/015107 A2 | 2/2007 |

OTHER PUBLICATIONS

Adelman et al., "Synergistic Inhibition of Platelet Aggregation by Fibrinogen-Related Peptides," *Circ Res.* 67(4):941-947, Oct. 1990.
Bar et al., "The binding of fibrin sealant to collagen is influenced by the method of purification and the cross-linked fibrinogen-fibronectin (heteronectin) content of the 'fibrinogen' component," *Blood Coagulation and Fibrinolysis* 16(2):111-117, 2005.
Binnie et al., "The Fibrinogen Sequences That Interact With Thrombin," *Blood* 81(12):3186-3192, Jun. 1993.
Chernysh et al., "Fibrin Clots Are Equilibrium Polymers That Can Be Remodeled Without Proteolytic Digestion," *Scientific Reports* 2:879, Nov. 2012, 7 pages.
Crawley et al., "The central role of thrombin in hemostasis," *Journal of Thrombosis and Haemostasis* 5(Suppl. 1):95-101, 2007.
Doolittle, Chapter 21, "Fibrinogen and fibrin," in *Haemostasis and Thrombosis*, 3rd Edition, vol. 1, Bloom et al. (eds.), Churchill Livingstone, New York, 1994, pp. 491-573.
Grunkemeier et al., "Fibrinogen Adsorption to Receptor-Like Biomaterials Made by Pre-adsorbing Peptides to Polystyrene Substrates," *Journal of Molecular Recognition* 9:247-257, 1996.
Hidas et al., "Sutureless Nephron-Sparing Surgery: Use of Albumin Glutaraldehyde Tissue Adhesive (BioGlue)," *Urology* 67(4):697-700, 2006.

(Continued)

*Primary Examiner* — Patricia Duffy
*Assistant Examiner* — Garen Gotfredson
(74) *Attorney, Agent, or Firm* — Seed IP Law Group LLP

(57) ABSTRACT

A biogel, and kits, agents, and methods for formation of the biogel are described. The biogel can be used for a variety of applications, including haemostasis, wound sealing, tissue engineering or localized drug delivery.

22 Claims, 4 Drawing Sheets

(56) References Cited

OTHER PUBLICATIONS

Kaczmarek et al. "Thrombin Binding to the Aα-, Bβ-, and γ-Chains of Fibrinogen and to Their Remnants Contained in Fragment E," *The Journal of Biological Chemistry* 263(27):13896-13900, Sep. 1988.

Laudano et al., "Synthetic peptide derivatives that bind to fibrinogen and prevent the polymerization of fibrin monomers," *Proc. Natl. Acad. Sci USA* 75(7):3085-3089, Jul. 1978.

Lin et al., "A Latent Inhibitor of Fibrin Polymerization with Ancillary Anticoagulant Activity," *Thrombosis Research* 97:375-378, 2000.

Martinowitz et al., "Fibrin Tissue Adhesives," *Thrombosis and Haemostasis* 78(1):661-666, 1997.

Mosesson et al., "The Structure and Biological Features of Fibrinogen and Fibrin" *Annals New York Academy of Sciences* 936:11-30, Jun. 2001.

Pierno et al., "FbsA-Driven Fibrinogen Polymerization: A Bacterial "Deceiving Strategy"," *Physical review Letters* 96:028108, Jan. 2006, 4 pages.

Pietrocola et al., "Multiple Interactions of FbsA, a Surface Protein from *Streptococcus agalactiae* with Fibrinogen: Affinity, Stoichiometry and Structural Characterization," *Biochemistry* 45(42):12840-12852, 2006.

Seljelid et al., "Biological Effects if the Immunomodulator ,$\beta 1\text{-}3_D$ Polyglucose are Strongly Potentiated by Conjugation to Biodegradable Microbeads," *Scand J Immunol* 45:683-687, 1997.

Voet et al., *Chapter 35*, "Molecular Physiology," in *Biochemistry* $3^{rd}$ Edition, Wiley, Hoboken, 2004, pp. 1-96.

Zhang et al., "Formation of Fibrinogen-Based Hydrogels Using Phototriggerable Displasmalogen Liposomes," *Bioconjugate Chem.* 13(3):640-646, 2002.

* cited by examiner (a)

(b)

(c)

(A)

(B)

a)

b)

BIOGEL

STATEMENT REGARDING SEQUENCE LISTING

The Sequence Listing associated with this application is provided in text format in lieu of a paper copy, and is hereby incorporated by reference into the specification. The name of the text file containing the Sequence Listing is 430160_403 D1_SEQUENCE_LISTING.txt. The text file is 5.4 KB, was created on Apr. 12, 2016, and is being submitted electronically via EFS-Web.

This invention relates to a biogel, and to kits, agents, and methods for formation of the biogel. In a preferred aspect the biogel is a tissue adhesive. The biogel or tissue adhesive can be used for a variety of applications, including haemostasis, wound sealing, tissue engineering or localised drug delivery.

During the clotting process, fibrinogen is converted to fibrin by thrombin. Fibrinogen comprises two sets of three different chains ($\alpha$, $\beta$, and $\gamma$), linked to each other by disulfide bonds. Together these chains form a central globular domain (the E domain) connected to two distal globular domains (the D domains). Thrombin cleaves four arginine-glycine peptide bonds in the central E domain of fibrinogen to release an A peptide from each of the two $\alpha$ chains, and a B peptide from each of the two $\beta$ chains. The A and B peptides are termed fibrinopeptides. A fibrinogen molecule devoid of these fibrinopeptides is called a fibrin monomer. Fibrin monomers spontaneously assemble into ordered fibrous arrays called fibrin. Fibrin is stabilised by the formation of covalent cross-links between the side chains of different molecules in the fibrin fibre. Peptide bonds are formed between specific glutamine and lysine side chains in a transamidation reaction that is catalysed by Factor XIIIa.

Once activated, platelets also form an essential part of a blood clot. Platelets adhere to an exposed wound surface and become activated. The platelet membrane glycoprotein GPIIb/IIIa undergoes a change in conformation, which allows it to bind fibrinogen. Fibrinogen can bind to more than one platelet, and so platelets aggregate together. Platelet aggregates form the basic architecture of the clot, formed within a mesh of fibrin.

Fibrin tissue adhesive (FTA) is the name given to products formed by mimicking the last step of the coagulation cascade to form a fibrin clot. Commercially available FTA kits rapidly produce strong, biodegradable gels that are used for haemostasis, drug delivery, and as surgical glues, and tissue sealants. Fibrinogen, Factor XIII, thrombin, and calcium ions are typically delivered via a syringe device that separates fibrinogen and Factor XIII from calcium ions and thrombin during storage. Mixing of the components during discharge from the syringe results in thrombinolysis of fibrinogen to create fibrin, which self-assembles into a gel that is later cross-linked by calcium ion-activated Factor XIII. However, many FTAs utilise bovine thrombin, which can induce anaphylactic and autoimmune responses in patients.

Zhang et al. (Bioconjugate Chem. 2002 (13): 640-646) describe formation of fibrinogen-based hydrogels by photoactivated release of calcium ions from liposomes, and subsequent activation of transglutaminase-catalyzed cross-linking of fibrinogen. However, formation of these hydrogels is complicated, and specialized formulation of liposome and Factor XIII is required.

Hidas et al. (Urology 67(4), 2006: 697-700) describe use of albumin glutaraldehyde tissue adhesive in sutureless nephron-sparing surgery. Bovine serum albumin and glutaraldehyde were admixed. Glutaraldehyde exposure causes the lysine molecules of the bovine serum albumin, extracellular matrix proteins, and cell surfaces to bind to each other, creating a strong covalent bond. A disadvantage of this adhesive, however, is that glutaraldehyde is toxic, and there is a risk that bovine serum albumin can induce an allergic reaction in patients.

There is, therefore, a need to provide gel or tissue adhesive which does not require use of toxic agents, which minimizes the risk of allergic reaction, and which is simple to produce from components which can readily be stored in a stable condition.

According to the invention there is provided a biogel kit (i.e. a kit for formation of a biogel), which comprises: a plurality of carriers, a plurality of fibrinogen binding moieties being immobilised to each carrier; and fibrinogen, wherein each molecule of fibrinogen can bind at least two fibrinogen binding moieties.

The term "biogel" is used herein to include a gel comprising one or more components that are natural or recombinant biological molecules (or chemically synthesised biological molecules), or that are derived from biological molecules (for example derivatives that retain one or more functions of a biological molecule).

A biogel can be formed by contacting the fibrinogen and the carriers. Because a plurality of fibrinogen binding moieties are immobilised to each carrier, and because each fibrinogen molecule can bind at least two of the fibrinogen binding moieties, the fibrinogen molecules become linked together via the carriers. Non-covalent bonds are formed between the fibrinogen molecules and the fibrinogen binding moieties.

Accordingly, there is also provided according to the invention a method of forming a biogel, which comprises contacting fibrinogen molecules with a plurality of carriers, wherein each carrier has a plurality of fibrinogen binding moieties immobilised to the carrier, and each molecule of fibrinogen can bind at least two fibrinogen binding moieties, so that the fibrinogen molecules become linked together via the carriers by formation of non-covalent bonds between the fibrinogen binding moieties and the fibrinogen molecules.

There is further provided according to the invention a biogel which comprises fibrinogen molecules and a plurality of carriers, wherein each carrier has a plurality of fibrinogen binding moieties immobilised to the carrier, and each molecule of fibrinogen is bound to at least two fibrinogen binding moieties, so that the fibrinogen molecules are linked together via the carriers by non-covalent bonds between the fibrinogen binding moieties and the fibrinogen molecules.

Instead of fibrinogen binding moieties, the carriers may have a plurality of fibrinogen binding precursors immobilised to each carrier, wherein each fibrinogen binding precursor can be converted to a fibrinogen binding moiety. To form a biogel using such carriers, it is necessary to convert the fibrinogen binding precursors to fibrinogen binding moieties so that the fibrinogen binding moieties can then bind to the fibrinogen molecules.

Accordingly there is also provided according to the invention a biogel kit (i.e. a kit for formation of a biogel), which comprises: a plurality of carriers, a plurality of fibrinogen binding precursors being immobilised to each carrier, wherein each fibrinogen binding precursor can be converted to a fibrinogen binding moiety; and fibrinogen, wherein each molecule of fibrinogen can bind at least two fibrinogen binding moieties.

There is further provided according to the invention a method of forming a biogel, which comprises: providing a plurality of carriers, each carrier comprising a plurality of fibrinogen binding precursors immobilised to the carrier; converting the fibrinogen binding precursors to fibrinogen binding moieties; and contacting fibrinogen molecules with the fibrinogen binding moieties, wherein each molecule of fibrinogen can bind at least two fibrinogen binding moieties, so that the fibrinogen molecules become linked together via the carriers by formation of non-covalent bonds between the fibrinogen binding moieties and the fibrinogen molecules.

A biogel of the invention need not be capable of adhering to a tissue substrate. However, in preferred aspects a biogel of the invention is a tissue adhesive. The term "tissue adhesive" is used herein to mean a substance that can adhere to a tissue substrate, for example skin, or a mucosal surface. Biogels or tissue adhesives of the invention may be used in haemostasis, as sealants, for tissue engineering (for example as a support), or for localised drug delivery.

The carrier may be a soluble or insoluble carrier, but is not a platelet. The carrier should be suitable for topical administration to a tissue site of a subject, for example a bleeding wound site, or a mucosal site. Soluble carrier may be suitable for intravenous rather than topical administration. The carrier may comprise a soluble or insoluble protein, a therapeutic drug, a polymer (for example a biocompatible polymer, such as polyethylene glycol), or a combination of any of these.

Examples of protein carriers are an enzyme or a protein which is not an enzyme, such as human serum albumin.

An insoluble carrier may be a microparticle (including a solid, hollow, or porous microparticle, preferably a substantially spherical microparticle). The microparticle may be formed of any suitable substance, for example cross-linked protein. A suitable protein is albumin (serum-derived or recombinant, human or non-human in sequence). Microparticles suitable for use as insoluble carriers in the present invention may be formed by spray drying human serum albumin using well known spray-drying technology, for example as in WO 92/18164.

Alternatives to use of microparticles as carriers include liposomes, synthetic polymer particles (such as polylactic acid, polyglycolic acid and poly(lactic/glycolic) acid), or cell membrane fragments.

The term "fibrinogen" is used herein to include natural fibrinogen, recombinant fibrinogen, or a derivative of fibrinogen that can be converted by thrombin to form fibrin (for example, natural or recombinant fibrin monomer, or a derivative of fibrin monomer that may or may not be capable of spontaneous assembly). The fibrinogen should be able to bind at least two fibrinogen binding moieties. The fibrinogen may be obtained from any source, and from any species (including bovine fibrinogen), but is preferably human fibrinogen. Human fibrinogen may be obtained from autologous or donor blood. Autologous fibrinogen is preferred because this reduces the risk of infection when biogel (or adhesive) of the invention is administered to a subject.

Preferably the fibrinogen binding moiety binds to fibrinogen with a dissociation constant ($K_D$) of between $10^{-9}$ to $10^{-6}$ M, for example around 10, 20, 30, 40, 50, 60, 70, 80, 90, 100, 110, 120, 130, 140, 150, 200, 250, 300, 350, 400, or more nM. A $K_D$ of around 100 nM is preferred. The dissociation constant can be measured at equilibrium. For example, radio-labelled fibrinogen of known concentration can be incubated with microspheres to which the fibrinogen binding moiety has been cross-linked. Typically 5 µM peptide is cross-linked to 1 gm microspheres, or 15-40 µmoles of peptide is cross-linked to 1 gm of microspheres. The peptide-linked microspheres are diluted to 0.5 mg/ml, and incubated in isotonic buffer at pH 7.4 (for example 0.01M Hepes buffer containing 0.15M NaCl) with radio labelled fibrinogen at concentrations of between 0.05 and 0.5 mg/ml for up to 1 hr at 20° C. The fibrinogen bound to the fibrinogen binding moiety on the microspheres can be separated from the free fibrinogen by centrifugation and the amount of free and bound fibrinogen measured. The dissociation constant can then be calculated by Scatchard analysis by plotting concentration of bound fibrinogen against the ratio of the concentrations of bound:free fibrinogen, where the slope of the curve represents $K_D$.

In some embodiments of the invention it is preferred that the fibrinogen binding moiety binds selectively to fibrinogen. In other embodiments it is preferred that the fibrinogen binding moiety can bind to fibrinogen, and separately to fibrin monomer and/or fibrin. Binding to fibrinogen and fibrin monomer and/or fibrin is preferably selective.

Preferably the fibrinogen binding moiety is a fibrinogen binding peptide or peptide analogue. Any suitable fibrinogen binding peptide may be used. For example, the peptide may be capable of binding to a region of fibrinogen that is naturally bound to fibrin or by the platelet membrane glycoproteins GPIIb-IIIa. Fibrin binding to fibrinogen is discussed in Mosesson et al. 2001, *Ann. N.Y. Acad. Sci.*, 936, 11-30. Binding of GPIIb-IIIa to fibrinogen is discussed in Bennett, 2001, *Annals of NY Acad. Sci.*, 936, 340-354.

The peptide may be capable of binding to the carboxy- and/or amino-terminal domain of the α-chain of fibrinogen. In particular, the peptide may be capable of binding to an RGD-containing motif in one or both of these domains (such as RGDF (SEQ ID NO: 1) at amino acids 95-98, or RGDS (SEQ ID NO: 2) at amino acids 572-575). The peptide may be capable of binding to the carboxy-terminal domain of the γ-chain of fibrinogen, preferably to the final 12 amino acids of this domain (sequence HHLGGAKQAGDV (SEQ ID NO: 3)). The peptide may be capable of binding to the D-domain of the γ-chain of fibrinogen, such as the β-chain segment of the D-domain.

The fibrinogen binding peptide may comprise a sequence derived from a fibrinogen-binding region of GPIIb or GPIIIa. For example, the peptide may comprise the sequence AVTDVNGDGRHDLLVGAPLYM (SEQ ID NO: 4) which corresponds to the sequence of amino acid residues 294-314 of GPIIb, or a fragment or derivative thereof that retains fibrinogen binding activity. Fragments known to retain fibrinogen binding activity are TDVNGDGRHDL (296-306) (SEQ ID NO: 5), GDGRHDLLVGAPL (300-312) (SEQ ID NO: 6), and GAPL (SEQ ID NO: 7). Suitable derivatives of TDVNGDGRHDL include: T(D,E)VNG(D,E)GRH(D,E)L (SEQ ID NO: 8); TD(V,L)NGDGRHDL (SEQ ID NO: 9); TDV(N,Q)GDGRHDL (SEQ ID NO: 10); TDVNGDG(R,K)HDL (SEQ ID NO: 11).

The fibrinogen binding peptide may comprise the sequence of residues 95-223 of GPIIIa, or a fragment or derivative thereof that retains fibrinogen binding activity. For example, residues 211-222, comprising the sequence SVSRNRDAPEGG (SEQ ID NO: 12), are thought to be an important fibrinogen-binding domain in GPIIIa. Other suitable regions of GPIIIa include residues 109-171 and 164-202.

The fibrinogen binding peptide may comprise the sequence of residues which becomes exposed on fibrinogen by the action of thrombin, and which binds fibrinogen as the first step in the polymerisation reaction to produce fibrin. Thrombin cleaves peptides (releasing fibrinopeptides A and B) from the N terminals of the α and β chains of fibrinogen to expose the sequences $NH_2$-GPR- (SEQ ID NO: 13) and NH$_2$-GHR- (SEQ ID NO: 14) respectively. A preferred example of a fibrinogen binding peptide therefore comprises the amino acid sequence NH$_2$-G(P,H)RX- (SEQ ID NO: 15) at its amino terminal end, where X is any amino acid, and (P,H) means that either proline or histidine is present at that position. Preferably the peptide comprises the sequence NH$_2$-GPRP- (SEQ ID NO: 16) at its amino terminal end.

Preferably the fibrinogen binding peptide is 4-30, more preferably 4-10, amino acid residues in length.

The fibrinogen binding precursor should not bind to fibrinogen such that fibrinogen molecules become linked together via carriers having immobilised fibrinogen binding precursors when the carriers are in contact with fibrinogen. Preferably the dissociation constant of the fibrinogen binding precursor for fibrinogen is greater than $1 \times 10^6$M. The fibrinogen binding precursor may be a peptide or a peptide analogue, but is preferably a peptide. The fibrinogen binding precursor should not be fibrinogen nor comprise fibrinogen.

In preferred embodiments of the invention the fibrinogen binding precursor comprises a fibrinogen binding peptide joined at its amino terminal end to a blocking component (preferably a peptide) that blocks or inhibits (i.e. reduces) binding of fibrinogen to the fibrinogen binding peptide. Cleavage of the fibrinogen binding precursor by a converting agent (preferably a coagulation factor such as thrombin) exposes the fibrinogen binding peptide bound to the carrier, thereby converting the fibrinogen binding precursor to a fibrinogen binding moiety. In such embodiments, the blocking component blocks or inhibits the ability of the fibrinogen binding peptide to bind fibrinogen until cleavage occurs. Preferably the blocking component is a peptide of 1-30 amino acid residues in length.

It will be appreciated that in such embodiments the fibrinogen binding precursor should comprise a cleavage site that is recognised specifically by the converting agent and which is located between the fibrinogen binding peptide and the blocking component. Thrombin is a preferred converting agent. However, other serine proteases or coagulation factors may be used to cleave the fibrinogen binding precursor. Thrombin is known to cleave peptide bonds carboxy-terminal to arginine residues, and commonly between arginine and glycine residues.

In particularly preferred embodiments of the invention the fibrinogen binding precursor is a peptide which comprises the amino acid sequence NH$_2$-ZYXR/GPRP- (SEQ ID NO: 17) at its amino terminal end, where "/" represents a thrombin cleavage site, and X is any amino acid, but is preferably proline, Y is any amino acid, but is preferably aspartic acid or alanine, and Z is at least one amino acid that is preferably leucine or proline. Examples are: NH$_2$-LVPR/GPRP- (SEQ ID NO: 18), NH$_2$-ADPR/GPRP- (SEQ ID NO: 19), NH$_2$-LDPR/GPRP- (SEQ ID NO: 20), or NH$_2$-LVPR/GPRV- (SEQ ID NO: 21).

The fibrinogen binding moieties or precursors can be bound to the carrier by any suitable means, but are typically covalently bound. Examples of preferred covalent bonds are a disulphide bond, a thioether bond, or an amide bond. A suitable covalent bond can be formed when the fibrinogen binding moieties or precursors are peptides which comprise a cysteine and the carrier comprises a thiol reactive group. This allows the peptide to be bound to the carrier by linking the —SH group of the cysteine to the thiol-reactive group on the carrier. Preferably a terminal cysteine group is incorporated in the fibrinogen binding peptide or precursor peptide to crosslink the peptide with a thiol-reactive group on the carrier. Alternatively, a covalent bond may be formed when the fibrinogen binding moiety or precursor is a peptide which comprises a maleimide group (preferably at its carboxy terminus, for example attached to a carboxy-terminal Lysine of the peptide), and the carrier comprises a sulphydryl group. The peptide may then be bound to the carrier by reacting the maleimide group of the peptide with the sulphydryl group of the carrier.

Typically, a spacer will be required between the fibrinogen binding moieties or precursors and the carrier to ensure that the fibrinogen-binding activity of the fibrinogen binding moieties (if necessary once converted from the fibrinogen binding precursors) is not adversely affected by the carrier. Suitable spacers are peptides, or non peptides such as polyethylene glycol.

Where the fibrinogen binding moieties or precursors are peptides which comprise a fibrinogen binding peptide, and the moieties or precursors are bound to the insoluble carrier by a terminal amino acid residue, a spacer sequence is preferably present between the terminal amino acid residue and the fibrinogen binding peptide of the moieties or precursors. The spacer sequence may, for example, be from 1-20, preferably 5-20, amino acid residues in length. The spacer sequence GGGGGG (SEQ ID NO: 22) or GGGGG (SEQ ID NO: 23) is preferred.

It will be appreciated that the number of fibrinogen binding moieties or precursors per carrier and the relative amounts of carrier (with a plurality of fibrinogen binding moieties or precursors per carrier) and fibrinogen required for optimal biogel (or tissue adhesive) formation may vary with different preparations of carrier and fibrinogen. Accordingly it may be necessary or desirable to test each new batch of carrier or fibrinogen to determine the optimum relative amounts of carrier and fibrinogen to use for biogel formation.

Preferably each carrier has on average at least five fibrinogen binding moieties or precursors per carrier. In theory there is no upper limit to the number of fibrinogen binding moieties or precursors per carrier. The optimum number is likely to depend on many factors, such as the nature of the carrier, and the number of reactive groups on each carrier for attaching the fibrinogen binding moities or precursors. However, it is preferred that each carrier has on average up to 100 fibrinogen binding moieties or precursors per carrier. A preferred range is 10-20 fibrinogen binding moieties or precursors per carrier.

Preferably the amount of fibrinogen used is such that there is at least one quarter (preferably at least one half) of the number of moles of fibrinogen present compared to the number of moles of fibrinogen binding moiety or precursor. Preferably the number of moles of fibrinogen relative to the number of moles of fibrinogen binding moiety or precursor is in the range 1:4 to 4:1.

Dynamic oscillatory measurements may be used to evaluate the viscoelastic properties of a biogel formed according to the invention. The storage (G') and loss modulus (G") in viscoelastic solids measure the stored energy, representing the elastic portion, and the energy dissipated as heat, representing the viscous portion. Tan delta is the ratio of the loss modulus (G") to the storage modulus (G'). It is therefore a quantification of the elastic and viscous contributions, where a value above 1 is indicative of liquid-like viscous behaviour, and a value below 1 signifies elastic behaviour. Biogels of the invention preferably have a tan delta value of less than 1. This provides an indication that the components of the gel are crosslinked. Tan delta may be determined at a frequency of 1 Hz and a constant strain of 1%. Suitable methods for measurement of tan delta are described in more detail in the examples below.

The components of a kit of the invention may be stored separately from each other, or some or all of the components of the kit may be stored together provided that components stored together will not react with each other. For embodiments of the invention in which the kit comprises carriers with immobilised fibrinogen binding moieties, it will be appreciated that the fibrinogen should be stored separately from the carriers so that it does not react with the carriers. An important advantage of kits of the invention that comprise fibrinogen and carriers with immobilised fibrinogen binding precursors that do not bind fibrinogen is that the carriers and fibrinogen can be stored together.

Components of a kit of the invention may be stored separately from each other in a device (for example a syringe) for delivery of the components to a tissue or other site. The device may be arranged so that the components contact each other as they are delivered at the tissue or other site.

A kit of the invention may include instructions on how to use the components of the kit to produce a biogel or tissue adhesive.

Kits of the invention have the advantages that no toxic agents are required, biogel (or tissue adhesive) is simple to produce using the components of the kits, and the components can readily be stored in a stable condition. It will also be appreciated that there is no requirement for thrombin (or other enzymes) to be present for formation of a biogel or tissue adhesive using a kit of the invention. Kits of the invention which do not include thrombin are particularly advantageous because the risk of allergic reaction to a biogel or tissue adhesive formed using such kits is reduced compared to biogel or tissue adhesive formed using exogenous thrombin. A further advantage of kits of the invention that do not include thrombin (or other enzymes) is that there is no requirement to store the components of the kit under conditions that preserve enzyme activity.

According to some embodiments of the invention, the fibrinogen binding precursors can be converted to fibrinogen binding moieties by a converting agent that is present at a site to which carriers having immobilised fibrinogen binding precursors are administered. This has the advantage that there is no requirement for the converting agent to be part of the kit. Consequently, there is no requirement to store the components of the kit under conditions that preserve activity of the converting agent.

Preferably the converting agent is a wound site agent. The term "wound site agent" is used herein to mean an agent which is present at a wound site. In a preferred embodiment the wound site agent is a coagulation factor. Examples of suitable coagulation factors include thrombin, Factor VIIa, Factor Xa, or Factor XIa. Preferably the coagulation factor is thrombin.

According to other embodiments, a kit of the invention may further comprise a converting agent for converting the fibrinogen binding precursors to fibrinogen binding moieties. The converting agent should be separate from the carrier. In such embodiments the converting agent may be an agent that is not expected to be present at a site to which the carriers are to be administered. Alternatively the converting agent may be an agent that is present at a site to which the carriers are administered. The converting agent may be a coagulation factor, such as thrombin, Factor VIIa, Factor Xa, or Factor XIa.

A kit of the invention comprising carriers with immobilised fibrinogen binding moieties may further comprise a coagulation factor. A kit of the invention comprising fibrinogen binding precursors that can be converted to fibrinogen binding moieties by a coagulation factor may comprise a coagulation factor which does not convert the fibrinogen binding precursors to fibrinogen binding moieties. In such embodiments the coagulation factor (that does not convert the fibrinogen binding precursors) may be provided as a separate component of the kit, or with the carrier and/or fibrinogen. The coagulation factor may be immobilised to the carrier, for example coupled to each fibrinogen binding precursor.

Where a kit of the invention comprises a coagulation factor (for example thrombin), this is preferably a coagulation factor which is of human sequence, rather than non-human (such as a bovine coagulation factor) to reduce the risk of allergic reaction to the coagulation factor.

A biogel or tissue adhesive of the invention may be formed before being administered to a tissue site, or in situ at a tissue site, for example at a wound site. Biogel or tissue adhesive at a tissue site preferably comprises topically administered carrier.

It will be appreciated that thrombin may be present at a tissue site at which a biogel or tissue adhesive of the invention is administered or formed. For example, if the tissue site is a bleeding wound site, host thrombin is likely to be present at the wound site. Of course, thrombin may alternatively or additionally be present if it is provided with a kit of the invention.

Use of fibrinogen binding moieties that are able to bind to fibrinogen and separately to fibrin monomer and/or fibrin may be advantageous if biogel or adhesive of the invention is formed in the presence of thrombin, or comes into contact with thrombin once it is formed. If thrombin is present with fibrinogen and carriers having immobilised fibrinogen binding moieties, the thrombin will convert at least some of the fibrinogen to fibrin monomer. It will be appreciated that under these conditions, it is preferred that the fibrinogen binding moieties also bind to fibrin monomers so that the fibrin monomers formed by thrombin can be linked together by the carriers.

If biogel or adhesive of the invention comes into contact with thrombin once it is formed, it may be advantageous if the fibrinogen bound to the fibrinogen binding moieties is able to be converted to fibrin monomer and the fibrinogen binding moieties remain bound to the fibrin monomer. Under these circumstances non-covalent bonds formed between fibrinogen and the fibrinogen binding moieties will not be disrupted by conversion of fibrinogen to fibrin monomer. It may also be advantageous if at least some of the fibrin monomers bound to the fibrinogen binding moieties are able to assemble to form fibrin whilst remaining bound to the fibrinogen binding moieties. Under these circumstances the biogel or tissue adhesive may be strengthened by the formation of fibrin.

If thrombin is present (for example, from a kit of the invention, or host thrombin at a wound site) it is preferred that the carriers and fibrinogen are contacted with each other before being contacted with thrombin, or that the carriers, fibrinogen and thrombin are contacted with each other at substantially the same time.

Whilst it is possible that a biogel or tissue adhesive may be formed if thrombin and fibrinogen are contacted with each other before contact with the carriers, this is expected to be of less use than a biogel or tissue adhesive formed by contacting the carriers and fibrinogen with each other before thrombin, or by contacting the carriers, fibrinogen and thrombin with each other at substantially the same time. This is because the thrombin will be expected to convert the fibrinogen molecules to fibrin monomers which will then aggregate to form insoluble fibrin before contact with the carriers. However, it may in some circumstances be appropriate to form a biogel or tissue adhesive by contacting the thrombin and fibrinogen before the carriers, for example if the thrombin is inactive until or after contact with the carriers.

There is also provided according to the invention a method of forming a biogel, which comprises contacting a plurality of carriers with fibrinogen molecules and thrombin, wherein a plurality of fibrinogen binding moieties are immobilised to each carrier, and each fibrinogen molecule can bind at least two fibrinogen binding moieties, to form a biogel in which fibrin monomers are linked together via the carriers by non-covalent bonds between the fibrinogen binding moieties and the fibrin monomers.

The biogel may or may not comprise fibrin. Accordingly, the fibrin monomers may be part of fibrin in the biogel, or the fibrin monomers may not be part of fibrin in the biogel.

There is also provided according to the invention a biogel which comprises fibrin monomers and a plurality of carriers, each carrier having a plurality of fibrinogen binding moieties immobilised to the carrier, wherein the fibrin monomers are linked together via the carriers by non-covalent bonds between the fibrinogen binding moieties and the fibrin monomers.

There is further provided according to the invention a biogel which comprises fibrin and a plurality of carriers, each carrier having a plurality of fibrinogen binding moieties immobilised to the carrier, wherein fibrin monomers of the fibrin are linked together via the carriers by non-covalent bonds between the fibrinogen binding moieties and the fibrin monomers.

In a preferred aspect the biogel is a tissue adhesive.

A kit of the invention may comprise Factor XIII, and optionally calcium ions and thrombin for activation of Factor XIII to Factor XIIIa (if so, the calcium ions and thrombin should be separate from the Factor XIII). Alternatively or additionally, Factor XIIIa may be present at a tissue site at which a biogel or tissue adhesive of the invention is administered or formed. For example, if the tissue site is a bleeding wound site, host Factor XIIIa is likely to be present at the wound site.

If Factor XIIIa is contacted with a biogel or tissue adhesive of the invention which comprises fibrin, the biogel or tissue adhesive may be further strengthened by reaction of Factor XIIIa with the fibrin to covalently cross-link the fibrin.

There is also provided according to the invention a method of forming a biogel, which comprises: contacting a plurality of carriers with fibrinogen molecules and thrombin, wherein a plurality of fibrinogen binding moieties are immobilised to each carrier, and each fibrinogen molecule can bind at least two fibrinogen binding moieties, to form a biogel comprising fibrin in which fibrin monomers of the fibrin are linked together via the carriers by non-covalent bonds between the fibrinogen binding moieties and the fibrin monomers; and contacting the biogel with Factor XIIIa so that fibrin monomers of the fibrin become covalently linked together by peptide bonds.

There is further provided according to the invention a biogel which comprises fibrin and a plurality of carriers, each carrier having a plurality of fibrinogen binding moieties immobilised to the carrier, wherein fibrin monomers of the fibrin are covalently linked together by peptide bonds and fibrin monomers of the fibrin are linked together via the carriers by non-covalent bonds between the fibrinogen binding moieties and the fibrin monomers.

In a preferred aspect the biogel is a tissue adhesive.

A kit of the invention may further comprise a promoter of wound healing. Suitable examples include growth factors, such as platelet-derived growth factor. The promoter may be a separate component of the kit, or immobilised to the carrier.

A kit of the invention may further comprise an antimicrobial agent, for example an antibiotic. The antimicrobial agent may be a separate component of the kit, or immobilised to the carrier.

It will be appreciated that if carriers having a plurality of fibrinogen binding moieties immobilised to each carrier are administered to a tissue site at which host fibrinogen is present (for example, at a bleeding wound site) the carriers will react with the host's fibrinogen to form a biogel or tissue adhesive in situ at the tissue site.

Similarly, if carriers having a plurality of fibrinogen binding precursors immobilised to each carrier are administered to a tissue site at which a converting agent for converting the fibrinogen binding precursors to fibrinogen binding moieties, and host fibrinogen are present (for example, at a bleeding wound site) the fibrinogen binding precursors will be converted to fibrinogen binding moieties, and the carriers will then react with the host's fibrinogen to form a biogel or tissue adhesive in situ at the tissue site. For example, the fibrinogen binding precursors may be converted to fibrinogen binding moieties by host thrombin, or another coagulation factor.

Accordingly, there is further provided according to the invention a biogel which comprises topically administered carriers, each carrier having a plurality of fibrinogen binding moieties immobilised to the carrier, and endogenous fibrinogen, wherein each molecule of endogenous fibrinogen is bound to at least two fibrinogen binding moieties, so that the fibrinogen molecules are linked together via the carriers by non-covalent bonds between the fibrinogen binding moieties and the endogenous fibrinogen molecules.

The term "endogenous fibrinogen" is used herein to mean that the fibrinogen is host fibrinogen, which is present at a site to which the carriers are administered. Typically the host fibrinogen will be present because blood of the host is present at the wound site.

There is also provided according to the invention use of a carrier for formation of a biogel, the carrier having a plurality of fibrinogen binding moieties or fibrinogen binding precursors immobilised to the carrier.

The biogel is preferably a tissue adhesive.

The carrier may be used for formation of a biogel or tissue adhesive for haemostasis, as a sealant, for localised drug delivery, or for tissue engineering.

Administration of a carrier to form a biogel or tissue adhesive has the advantage that the risk of host allergic reaction is minimised because there is no requirement for exogenous fibrinogen or thrombin, no toxic agents are required, and the carrier can readily be stored in a stable condition.

There is also provided according to the invention a method of controlling bleeding at a site at which host fibrinogen is present, which comprises topically administering a plurality of carriers to the site, wherein each carrier has a plurality of fibrinogen binding moieties immobilised to the carrier, and host fibrinogen molecules at the site can bind at least two of the fibrinogen binding moieties.

There is further provided according to the invention a method of controlling bleeding at a site at which host fibrinogen and coagulation factor is present, which comprises topically administering a plurality of carriers to the site, wherein each carrier has a plurality of fibrinogen binding precursors immobilised to the carrier and the fibrinogen binding precursors can be converted to fibrinogen binding moieties by host coagulation factor, and host fibrinogen molecules at the site can bind at least two of the fibrinogen binding moieties.

There is further provided according to the invention use of a plurality of carriers in the manufacture of a medicament (e.g. a biogel or tissue adhesive) for controlling bleeding, or for treating or sealing a wound, wherein each carrier has a plurality of fibrinogen binding moieties or fibrinogen binding precursors immobilised to the carrier.

There is also provided according to the invention use of a plurality of carriers, each carrier having a plurality of fibrinogen binding moieties or fibrinogen binding precursors immobilised to the carrier, for formation of a biogel.

There is further provided according to the invention a plurality of carriers for use (e.g. as a biogel or tissue adhesive) in controlling bleeding, or for treating or sealing a wound, wherein each carrier has a plurality of fibrinogen binding moieties or fibrinogen binding precursors immobilised to the carrier.

The carriers may be insoluble or soluble. Carriers may be administered topically.

If the carrier is a soluble carrier, a preferred topical formulation of the carrier having immobilised fibrinogen binding moieties or fibrinogen binding precursors is a liquid formulation, preferably in an isotonic buffer at physiological pH.

If the carrier is an insoluble carrier, a preferred topical formulation of the carrier having immobilised fibrinogen binding moieties or fibrinogen binding precursors is in the form of a powder that can be sprayed, for example, onto a tissue site.

Powdered carrier may be formed using any suitable method, including methods comprising spray drying, or lyophilising a suspension of carrier having a plurality of fibrinogen binding moieties or fibrinogen binding precursors immobilised to each carrier (for example suspended in an isotonic buffer at physiological pH). Preferably spray-drying is used since this can be a more rapid and easily scaled method of drying than lyophilisation. Suitable spray-drying methods are described in WO 92/18164.

According to the invention there is provided an agent for formation of a biogel, the agent comprising soluble carrier, wherein a plurality of fibrinogen binding moieties or fibrinogen binding precursors are immobilised to each carrier.

There is also provided according to the invention an agent for formation of a biogel, the agent comprising insoluble carrier having a plurality of fibrinogen binding moieties or fibrinogen binding precursors immobilised to each carrier, wherein the agent is in the form of a powder formed other than by lyophilisation.

There is also provided according to the invention a method of forming a powdered agent, the agent comprising insoluble carrier having a plurality of fibrinogen binding moieties or fibrinogen binding precursors immobilised to each carrier, wherein the method comprises spray-drying a suspension of the agent.

Preferably the agent is suitable for topical administration. If the agent comprises soluble carrier with a plurality of fibrinogen binding precursors immobilised to each carrier, the agent may be suitable for intravenous administration.

The carrier or agent may be provided as a component of a kit. The kit may further comprise a coagulation factor, a promoter of wound healing, or an antimicrobial agent. The coagulation factor, promoter of wound healing, or antimicrobial agent may be a separate component of the kit, or immobilised to the carrier. In some preferred embodiments the coagulation factor, promoter of wound healing, or antimicrobial agent may be part of the fibrinogen binding precursor such that it is released when the fibrinogen binding precursor is converted to a fibrinogen binding moiety.

A kit of the invention may be a compartmentalised kit in which components of the kit that are desired to be kept separate from one another are contained in separate compartments or containers. A kit of the invention may include instructions for using the kit components to carry out a method of the invention.

Biogel or tissue adhesive of the invention may be topically administered to a tissue site, for example to skin or mucosal tissue. Biogel or tissue adhesive of the invention may be used for haemostasis, as a sealant, for localized drug delivery or for tissue engineering.

Biogel or tissue adhesive of the invention may be administered by forming the gel or adhesive before contacting the gel or adhesive with the administration site, or by forming the biogel or tissue adhesive at the administration site.

It has also been appreciated that an agent comprising soluble carrier, wherein a plurality of fibrinogen binding precursors each of which can be converted to a fibrinogen binding moiety, are immobilised to each carrier may be administered intravenously, for example to control bleeding or for drug delivery. A preferred intravenous formulation is a 20% aqueous isotonic solution. In a preferred embodiment, the fibrinogen binding precursors can be converted by thrombin.

There is further provided according to the invention a method of controlling bleeding, which comprises intravenously administering an agent comprising soluble carrier, wherein a plurality of fibrinogen binding precursors each of which can be converted to a fibrinogen binding moiety, are immobilised to each carrier.

There is further provided according to the invention a method of delivering a drug to a subject, which comprises intravenously administering an agent comprising soluble carrier to the subject, wherein a plurality of fibrinogen binding precursors each of which can be converted to a fibrinogen binding moiety, are immobilised to each carrier, and wherein the carrier comprises a drug or a drug is immobilised to the carrier.

Of course topical or intravenous formulations should be sterile.

Biogel or tissue adhesive of the invention may further comprise a promoter of wound healing, or an antimicrobial agent.

There is also provided according to the invention a method of controlling bleeding, which comprises topically administering biogel or tissue adhesive of the invention to a bleeding site.

There is also provided according to the invention a method of treating or sealing a wound, which comprises administering (preferably topically) a biogel or tissue adhesive of the invention to a wound site.

There is also provided according to the invention a biogel or tissue adhesive of the invention for use as a medicament.

There is further provided according to the invention use of a biogel or tissue adhesive of the invention in the manufacture of a medicament for controlling bleeding, or for treating or sealing a wound.

There is also provided according to the invention a biogel or tissue adhesive of the invention for controlling bleeding, or for treating or sealing a wound.

Use of a biogel or tissue adhesive of the invention may be topical use. Where the biogel or tissue adhesive is formed with soluble carrier and fibrinogen binding moieties converted from fibrinogen binding precursors, the use may be intravenous.

Preferred embodiments of the invention are now described by way of example only.

According to a first preferred embodiment of the invention, a plurality of peptides, each comprising a fibrinogen binding sequence at the amino-terminal end (for example peptides of sequence GPRPGGGGGGC (SEQ ID NO: 24)) are linked at their carboxy-terminal ends to a carrier, which is a soluble protein (such as albumin). A biogel is formed by contacting the peptide-linked carrier with fibrinogen. The biogel may then be administered topically as a dressing to a wound.

According to a second preferred embodiment of the invention, the peptide-linked carrier of the first preferred embodiment and fibrinogen are mixed at a wound site to form a biogel in situ.

According to a third preferred embodiment of the invention, the peptide-linked carrier of the first preferred embodiment is administered to a wound site at which fibrinogen from host blood is present to form a biogel in situ.

According to a fourth preferred embodiment of the invention, a plurality of peptides, each comprising a fibrinogen binding sequence coupled at its amino terminal end to a blocking peptide sequence (for example peptides of sequence LVPRGPRPGGGGGGC (SEQ ID NO: 25)), are linked at their carboxy-terminal ends to a carrier, which is a soluble protein (such as albumin). The peptide-linked carrier can be combined with fibrinogen and then applied to a wound as a single mixture. Host thrombin present at the site of the wound cleaves the peptides to release the blocking peptides and expose the fibrinogen binding sequence. The carrier with exposed fibrinogen binding sequence reacts with the fibrinogen to form a biogel in situ.

Alternatively, the peptide-linked carrier of the fourth preferred embodiment can be administered intravenously. Host thrombin at the site of a wound cleaves the peptides to release the blocking peptides and expose the fibrinogen binding sequence. The carrier with exposed fibrinogen binding sequences reacts with host fibrinogen to control bleeding at the wound site.

The biogel of the four preferred embodiments described above may be a tissue adhesive.

An insoluble carrier (for example an albumin microsphere) may be used instead of the soluble protein carrier in any of the above preferred embodiments (other than for intravenous administration).

Branched polyethylene glycol (PEG) or any other biocompatible polymer may be used instead of the soluble protein carrier in any of the above preferred embodiments.

A coagulation factor may be immobilised to the carrier in any of the above preferred embodiments, providing that where fibrinogen binding precursors are immobilised to the carrier, the coagulation factor will not convert the fibrinogen binding precursors to fibrinogen binding moieties.

The carrier may further comprise a promoter of wound healing (for example, a growth factor such as platelet-derived growth factor) in any of the above preferred embodiments.

Further preferred embodiments of the invention are described in the following examples with reference to the accompanying drawings in which:

FIG. 1 which shows schematically: (a) an albumin carrier having a plurality of fibrinogen binding peptides immobilised to the carrier; (b) a fibrinogen molecule; and (c) a biogel in which the fibrinogen molecules are linked together via the carriers by non-covalent bonds between the fibrinogen binding peptides and the fibrinogen molecules;

EXAMPLE 1

Formation of a Biogel or Tissue Adhesive Using Fibrinogen, and Fibrinogen Binding Peptides Immobilised to a Carrier Comprising Human Serum Albumin Human serum albumin (HSA) was reacted with a 40-fold molar excess of the linker succinimidyl-4-(N-maleimidomethyl)cyclohexane-1-carboxylate (SMCC) at pH 7.4. The modified protein (HSA-SMCC) was purified and it was determined that on average one mole of HSA was modified with 18 moles of SMCC. Either GPRPGGGGGGC (B10; SEQ ID NO: 24) or LVPRGPRPGGGGGGC (TC-15; SEQ ID NO: 25) peptide was added to HSA-SMCC at 1.5 mole excess in relation to maleimide moieties. The peptide-modified HSA protein was then purified from un-reacted peptide and stored at −80° C. at 7 mg/ml. Lyophilised human fibrinogen was solubilized in water at 16 mg/ml as described by supplier (Scottish National Blood Transfusion service).

Figure 1:
Figure 1:
Figure 1:
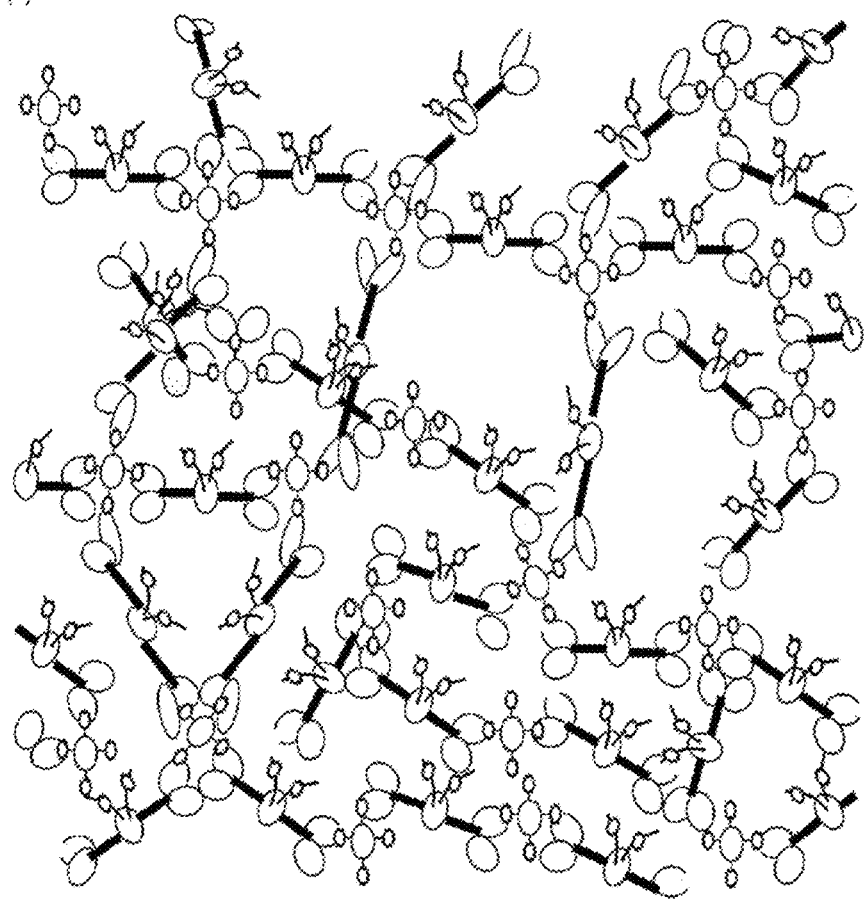

Peptide-modified HSA (5 μl) was added to 0.3 ml of fibrinogen solution, an instant gel was observed for B10-HSA while for TC-15 no gel was observed. The exposed GPRP peptide sequence is known to bind to the "a" pocket within the carbonyl region of the two distal domains (D) of fibrinogen (FIG. 1b). It is believed that the HSA modified with multiple exposed GPRP sequences (B10) acts as a branching point for polymerisation of fibrinogen (FIG. 1c). The gel is formed in the absence of thrombin.

Methods for Examples 2-5

Synthesis of Peptide-Modified HSA

Human serum albumin (HSA) at 10 mg/ml was reacted with a 5, 10, 20 or 40-fold molar excess of the linker sulfosuccinimidyl-4-(N-maleimidomethyl)cyclohexane-1-carboxylate (Sulfo-SMCC) at pH 7.4 with a total volume of 0.7 ml. The modified protein (HSA-SMCC) was purified by a Zebra™ Desalt Spin Column (Pierce, Rockford, Ill.) and it was determined that on average one mole of HSA was modified with 5, 8, 16 or 18 moles of Sulfo-SMCC, respectively. To determine the number of maleimide groups bound per HSA molecule, a sample of 3 nmoles of HSA was incubated with a known amount of cysteine (100 nmoles) in buffer at room temperature for 30 min. The remaining cysteine was then reacted with 1 mmol of 5,5-dithiobis(2-nitrobenzoate) (DTNB) for 20 min and $A_{412}$ was measured. The maleimide level was calculated by comparing the absorbance of the control and protein samples. Either GPRPGGGGGGC (B10; SEQ ID NO: 24) or LVPRG-PRPGGGGGGC (TC-15; SEQ ID NO: 25) peptide was added to HSA-SMCC at 1.5 mole excess in relation to maleimide moieties. The peptide-modified HSA protein was then purified from un-reacted peptide using a Zebra™ Desalt Spin Column (Pierce, Rockford, Ill.) and stored at −80° C. at 7 mg/ml. Lyophilised human fibrinogen (Scottish National Blood Transfusion Service, Edinburgh, Scotland) was solubilised in water at 8, 16, 32 and 64 mg/ml. The concentration of fibrinogen and albumin was determined from the absorbance at 280 nm ($A_{280}$) using a conversion factor of 1% Fibrinogen $E_{280}$=15 and 1% HSA $E_{280}$=13.8

Rheological Characterization

Dynamic oscillatory measurements were used to evaluate the viscoelastic properties of the gels. The mixture was allowed to equilibrate at room temperature overnight and the gel was transferred to the lower plate of a Physica MCR-501 (Anton Paar, Germany) rheometer with a cone and plate of 25 mm diameter and a 1° cone angle. Tests were performed at either 20 or 37±° C. in a humidified atmosphere. Frequency sweeps were performed between 0.01 and 50 Hz at a constant strain amplitude of 1%. The rheological parameters examined were processed with the dedicated Anton Paar software provided with the rheometer.

EXAMPLE 2

Influence of Both the Amount of Peptide-Modified HSA and Fibrinogen Concentration on Gel Formation The polymerisation of fibrinogen was initially monitored visually after the mixing of fibrinogen with HSA solutions. Peptide-modified HSA modified with either 5, 8, 16 or 18 moles of fibrinogen binding peptide was conjugated to one mole of HSA. A 25 ul sample of the peptide-modified HSA or unmodified HSA was mixed with 0.2 ml of fibrinogen at 8, 16, 32 or 64 mg/ml. The formation of a gel was visually determined after 0.5 h at room temperature. For unmodified HSA or HSA modified with 5 or 8 moles of peptide no gel formation was observed at all fibrinogen concentrations tested. Polymerisation was only observed at 32 or 64 mg/ml fibrinogen with peptide-modified HSA with 16 or 18 moles of binding peptide.

Figure 4:
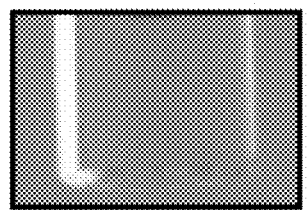
FIG. 4 shows a photograph of a fibrinogen solution before (a) and after (b) addition of peptide-modified HSA.
Figure 4:
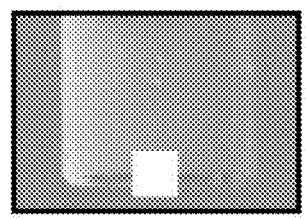

FIG. 4 shows a photograph of the fibrinogen solution (0.2 ml 32 mg/ml fibrinogen) before (a) and after (b) the addition of peptide-modified HSA (25 μl, 18 moles peptide). The biogel formed according to the invention is shown in (b).

EXAMPLE 3

Influence of the Amount of Peptide-Modified HSA

Figure 2:
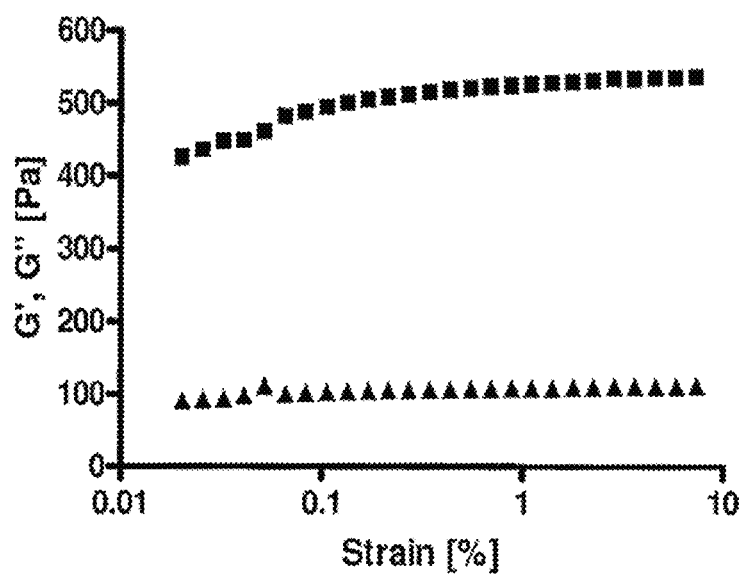
FIG. 2 shows a plot of the storage (squares) and loss modulus (triangles) against percentage strain on a mixture of 25 ul of peptide-modified HSA and fibrinogen at 32 mg/ml at 20° C. (A) and 37° C. (B)
Figure 2:
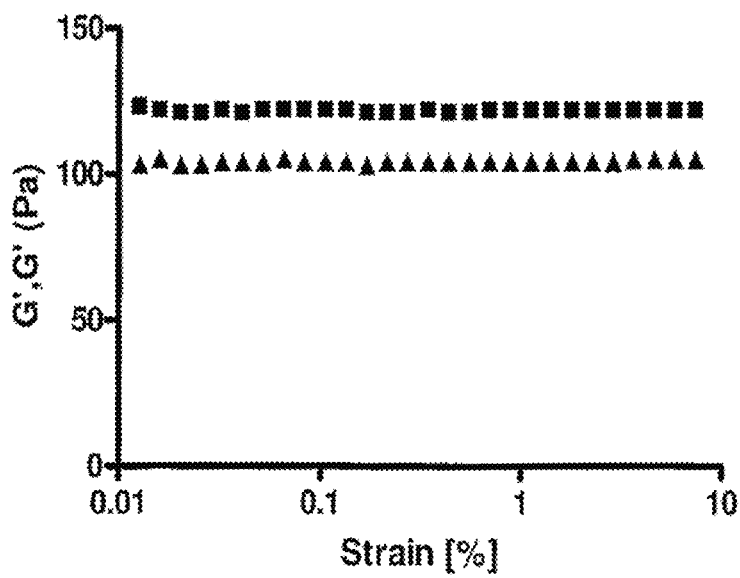
Figure 3:
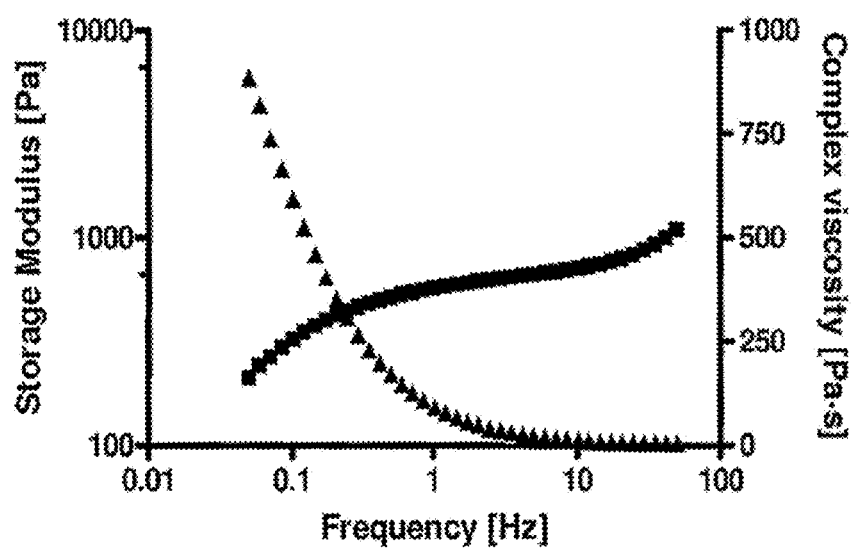
FIG. 3 shows storage modulus (squares) and complex viscosity (triangles) versus frequency at 20° C. (with 1% strain amplitude), for 25 ul of peptide-modified HSA mixed with fibrinogen at 32 mg/ml.

To determine the effect of the amount of peptide-modified HSA and fibrinogen on the rheological properties of the mixtures, shear strength measurements were determined with 25 or 50 ul of peptide-modified HSA with fibrinogen at 32 and 64 mg/ml. Peptide-modified HSA that was modified with 16 moles of binding-peptide per mole of HSA was used for this experiment. To ensure that the dynamic oscillatory experiments were made within the linear viscoelastic strain limit of the gel a strain sweep was performed. FIG. 2 shows the strain sweeps at 20 and 37° C. for 25 ul of peptide-modified HSA mixed with fibrinogen at 32 mg/ml. Both storage modulus (G') and loss modulus (G") appeared stable over the range and a constant strain of 1% was selected with in this linear viscoelastic strain range. Frequency sweeps demonstrated a G' value which was greater than G" which is indicative of a cross-linked network (Table 1). Values shown in this Table are taken at a frequency of 1 Hz. Tan delta is the ratio of the loss modulus to the storage modulus. It is therefore a quantification of the elastic and viscous contributions, where a value above 1 is indicative of liquid like viscous behaviour and below 1 signifies elastic behaviour. Complex viscosity $\eta^*$, defined as complex modulus $G^*$ divided by angular frequency ($\omega$), were determined under the same conditions. It appears under these conditions that amount of both peptide-modified HSA and fibrinogen does not influence greatly the mechanical strength of the gel.

TABLE 1

|  | Fibrinogen (mg/ml) | | | |
| --- | --- | --- | --- | --- |
|  | 32 | | 64 | |
| Peptide-modified HSA (ul) | 25 | 50 | 25 | 50 |
| Storage modulus (G') | 432 | 439 | 421 | 588 |
| Complex viscosity ($\eta^*$) | 88 | 70 | 77 | 94 |
| Tan delta | 0.22 | 0.11 | 0.24 | 0.2 |

A different batch of peptide-modified HSA with 18 peptides bound per HSA (25 ul) with 32 mg/ml fibrinogen showed G' of 5200, complex viscosity of 820 and Tan delta 0.105.

EXAMPLE 4

Influence of Temperature on Rheological Properties

Investigations of the effect of temperature on a gel are important for applications of the product when used at surgical body temperature or when applied topically.

We evaluated the mechanical strength of the gel at 20 and 37° C. and values given in Table 2 are taken at a frequency of 1 Hz. Increasing the temperature of the gel generated from fibrinogen at 32 mg/ml and 25 uL of HSA modified with 16 moles of peptide resulted in both a decrease in the G' and complex viscosity (Table 2). At both 20 and 37° C. the tan delta was below 1, therefore a (non-covalent) cross-linked network structure is maintained at 37° C.

TABLE 2

|  | Temperature (° C.) | |
| --- | --- | --- |
|  | 20 | 37 |
| Storage modulus (G') | 432 | 109 |
| Complex viscosity ($\eta^*$) | 88 | 21 |
| Tan delta | 0.22 | 0.72 |

EXAMPLE 5

Gel Formation in Human Plasma

Investigating whether the peptide-modified HSA could polymerise fibrinogen in human plasma is important for applications of the product as a surgical glue/adhesive. Peptide-modified HSA (75 ul) modified with 18 moles of peptide was mixed with 0.8 ml of human pooled plasma. Rheology on the plasma derived gel was performed at 37° C. and gave a G' value of 6100 with a tan delta of 0.104. It is concluded from this result that peptide-modified HSA can polymerise fibrinogen in human plasma resulting a in (non-covalent) cross-linked network structure at 37° C.

The invention claimed is:

1. A soluble agent for formation of a biogel, comprising one or more soluble carriers to each of which are covalently immobilized a plurality of fibrinogen binding moieties,
wherein each carrier comprises at least one of i) a protein and ii) a biocompatible polymer,
wherein each fibrinogen binding moiety is a peptide comprising the amino acid sequence NH2-G(P,H)RX- as set forth in SEQ ID NO: 15 at its amino terminal end, where X is any amino acid and either proline or histidine is present at position (P,H) in said amino acid sequence, and
wherein the agent, upon being contacted with a plurality of fibrinogen molecules when thrombin is absent, is capable of forming a biogel which comprises fibrinogen molecules and a plurality of carriers such that (i) each of said plurality of fibrinogen molecules binds at least two fibrinogen binding moieties, and (ii) in the biogel, the fibrinogen molecules are linked together via the carriers by non-covalent bonds between the fibrinogen binding moieties and the fibrinogen molecules.

2. The agent of claim 1, wherein the carrier comprises albumin.

3. The agent of claim 2, wherein the albumin of the carrier is human serum albumin.

4. The agent of claim 1, wherein the carrier comprises polyethylene glycol.

5. The agent of claim 1, wherein each fibrinogen binding moiety comprises the amino acid sequence NH$_2$-GPRP- as set forth in SEQ ID NO:16 at its amino terminal end.

6. The agent of claim 1, wherein each fibrinogen binding moiety is 4-30 amino acid residues in length.

7. The agent of claim 1, wherein each fibrinogen moiety is 4-10 amino acid residues in length.

8. The agent of claim 1, wherein each fibrinogen binding moiety is immobilized to the carrier via a non-peptide spacer.

9. The agent of claim 8, wherein the non-peptide spacer comprises polyethylene glycol.

10. The agent of claim 1, wherein each carrier has on average at least five fibrinogen binding moieties per carrier.

11. The agent of claim 1 which is provided in a liquid formulation.

12. The agent of claim 11, wherein the liquid formulation is a sterile formulation suitable for topical administration to a subject.

13. The agent of claim 1, wherein the carrier comprises albumin, and wherein each fibrinogen binding moiety comprises the amino acid sequence NH$_2$-GPRP- as set forth in SEQ ID NO:16 at its amino terminal end.

14. The agent of claim 1, wherein the carrier comprises albumin and wherein each fibrinogen binding moiety is 4-30 amino acid residues in length.

15. The agent of claim 1, wherein the carrier comprises albumin, wherein each fibrinogen binding moiety comprises the amino acid sequence NH$_2$-GPRP- as set forth in SEQ ID NO:16 at its amino terminal end, and wherein each fibrinogen binding moiety is 4-30 amino acid residues in length.

16. The agent of claim 1, wherein the carrier comprises albumin, wherein each fibrinogen binding moiety comprises the amino acid sequence NH$_2$-GPRP- as set forth in SEQ ID NO:16 at its amino terminal end, wherein each fibrinogen binding moiety is 4-30 amino acid residues in length and wherein each fibrinogen binding moiety is immobilized to the carrier via a non-peptide spacer.

17. A biogel which comprises fibrinogen molecules and a plurality of soluble carriers, wherein each soluble carrier has a plurality of fibrinogen binding moieties covalently immobilized to the soluble carrier, and each molecule of fibrinogen is bound to at least two fibrinogen binding moieties, so that the fibrinogen molecules are linked together via the soluble carriers by non-covalent bonds between the fibrinogen binding moieties and the fibrinogen molecules, wherein each soluble carrier comprises at least one of i) a protein and ii) a biocompatible polymer, and wherein each fibrinogen binding moiety is a peptide comprising the amino acid sequence NH2-G(P,H)RX- as set forth in SEQ ID NO: 15 at its amino terminal end, wherein the biogel is formed by contacting (i) said soluble carriers to which said plurality of fibrinogen binding moieties are covalently immobilized with (ii) a plurality of fibrinogen molecules when thrombin is absent.

18. A method of forming a biogel which comprises contacting fibrinogen molecules with the agent for formation of a biogel of claim 1.

19. A method of controlling bleeding, which comprises topically administering the agent of claim 1 to a bleeding site.

20. A method of controlling bleeding, which comprises topically administering the biogel of claim 17 to a bleeding site.

21. A method of treating or sealing a wound, which comprises topically administering the agent of claim 1 to a wound site.

22. A method of treating or sealing a wound, which comprises topically administering the biogel of claim 17 to a wound site.

* * * * *

UNITED STATES PATENT AND TRADEMARK OFFICE
CERTIFICATE OF CORRECTION

PATENT NO. : 9,913,876 B2
APPLICATION NO. : 15/098028
DATED : March 13, 2018
INVENTOR(S) : Greg Walker Page 1 of 1

It is certified that error appears in the above-identified patent and that said Letters Patent is hereby corrected as shown below:

On the Title Page

Item (56) References Cited:
"Grunkemeier et al., "Fibrinogen Adsorption to Receptor-Like Biomaterials Made by Pre-adsorbing Peptides to Polystyrene Substrates," *Journal ofMolecular Recognition 9*:247-257, 1996." should read, --Grunkemeier et al., "Fibrinogen Adsorption to Receptor-Like Biomaterials Made by Pre-adsorbing Peptides to Polystyrene Substrates," *Journal of Molecular Recognition 9*:247-257, 1996.--

Page 2, Column 2, Item (56) References Cited:
"Pierno et al., "FbsA-Driven Fibrinogen Polymerization: A Bacterial "Deceiving Strategy"," *Physical review Letters 96*:028108, Jan. 2006, 4 pages." should read, --Pierno et al., "FbsA-Driven Fibrinogen Polymerization: A Bacterial "Deceiving Strategy"," *Physical Review Letters 96*:028108, Jan. 2006, 4 pages.--

Signed and Sealed this
Eighteenth Day of June, 2019

Andrei Iancu
*Director of the United States Patent and Trademark Office*

SEQUENCE LISTING

<160> NUMBER OF SEQ ID NOS: 25

<210> SEQ ID NO 1
<211> LENGTH: 4
<212> TYPE: PRT
<213> ORGANISM: Homo sapiens

<400> SEQUENCE: 1

Arg Gly Asp Phe
1

<210> SEQ ID NO 2
<211> LENGTH: 4
<212> TYPE: PRT
<213> ORGANISM: Homo sapiens

<400> SEQUENCE: 2

Arg Gly Asp Ser
1

<210> SEQ ID NO 3
<211> LENGTH: 12
<212> TYPE: PRT
<213> ORGANISM: Homo sapiens

<400> SEQUENCE: 3

His His Leu Gly Gly Ala Lys Gln Ala Gly Asp Val
1               5                   10

<210> SEQ ID NO 4
<211> LENGTH: 21
<212> TYPE: PRT
<213> ORGANISM: Homo sapiens

<400> SEQUENCE: 4

Ala Val Thr Asp Val Asn Gly Asp Gly Arg His Asp Leu Leu Val Gly
1               5                   10                  15

Ala Pro Leu Tyr Met
            20

<210> SEQ ID NO 5
<211> LENGTH: 11
<212> TYPE: PRT
<213> ORGANISM: Homo sapiens

<400> SEQUENCE: 5

Thr Asp Val Asn Gly Asp Gly Arg His Asp Leu
1               5                   10

<210> SEQ ID NO 6
<211> LENGTH: 13
<212> TYPE: PRT
<213> ORGANISM: Homo sapiens

<400> SEQUENCE: 6

Gly Asp Gly Arg His Asp Leu Leu Val Gly Ala Pro Leu
1               5                   10

<210> SEQ ID NO 7
<211> LENGTH: 4
<212> TYPE: PRT
<213> ORGANISM: Homo sapiens

<400> SEQUENCE: 7

Gly Ala Pro Leu
1

<210> SEQ ID NO 8
<211> LENGTH: 11
<212> TYPE: PRT
<213> ORGANISM: Artificial Sequence
<220> FEATURE:
<223> OTHER INFORMATION: Peptide derivative
<220> FEATURE:
<221> NAME/KEY: MISC_FEATURE
<222> LOCATION: (2)..(2)
<223> OTHER INFORMATION: Asp or Glu
<220> FEATURE:
<221> NAME/KEY: MISC_FEATURE
<222> LOCATION: (6)..(6)
<223> OTHER INFORMATION: Asp or Glu
<220> FEATURE:
<221> NAME/KEY: MISC_FEATURE
<222> LOCATION: (10)..(10)
<223> OTHER INFORMATION: Asp or Glu

<400> SEQUENCE: 8

Thr Xaa Val Asn Gly Xaa Gly Arg His Xaa Leu
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Peptide derivative
<220> FEATURE:
<221> NAME/KEY: MISC_FEATURE
<222> LOCATION: (3)..(3)
<223> OTHER INFORMATION: Val or Leu

<400> SEQUENCE: 9

Thr Asp Xaa Asn Gly Asp Gly Arg His Asp Leu
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Peptide derivative
<220> FEATURE:
<221> NAME/KEY: MISC_FEATURE
<222> LOCATION: (4)..(4)
<223> OTHER INFORMATION: Asn or Gln

<400> SEQUENCE: 10

Thr Asp Val Xaa Gly Asp Gly Arg His Asp Leu
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Peptide derivative
<220> FEATURE:
<221> NAME/KEY: MISC_FEATURE
<222> LOCATION: (8)..(8)
<223> OTHER INFORMATION: Arg or Lys

<400> SEQUENCE: 11

Thr Asp Val Asn Gly Asp Gly Xaa His Asp Leu
1               5                   10

<210> SEQ ID NO 12
<211> LENGTH: 12
<212> TYPE: PRT
<213> ORGANISM: Homo sapiens

<400> SEQUENCE: 12

Ser Val Ser Arg Asn Arg Asp Ala Pro Glu Gly Gly
1               5                   10

<210> SEQ ID NO 13
<211> LENGTH: 3
<212> TYPE: PRT
<213> ORGANISM: Homo sapiens

<400> SEQUENCE: 13

Gly Pro Arg
1

<210> SEQ ID NO 14
<211> LENGTH: 3
<212> TYPE: PRT
<213> ORGANISM: Homo sapiens

<400> SEQUENCE: 14

Gly His Arg
1

<210> SEQ ID NO 15
<211> LENGTH: 4
<212> TYPE: PRT
<213> ORGANISM: Artificial Sequence
<220> FEATURE:
<223> OTHER INFORMATION: Peptide derivative
<220> FEATURE:
<221> NAME/KEY: MISC_FEATURE
<222> LOCATION: (2)..(2)
<223> OTHER INFORMATION: Pro or His
<220> FEATURE:
<221> NAME/KEY: MISC_FEATURE
<222> LOCATION: (4)..(4)
<223> OTHER INFORMATION: Any amino acid

<400> SEQUENCE: 15

Gly Xaa Arg Xaa
1

<210> SEQ ID NO 16
<211> LENGTH: 4
<212> TYPE: PRT
<213> ORGANISM: Artificial Sequence
<220> FEATURE:
<223> OTHER INFORMATION: Peptide derivative

<400> SEQUENCE: 16

Gly Pro Arg Pro
1

<210> SEQ ID NO 17
<211> LENGTH: 8
<212> TYPE: PRT
<213> ORGANISM: Artificial Sequence
<220> FEATURE:
<223> OTHER INFORMATION: Peptide derivative
<220> FEATURE:
<221> NAME/KEY: MISC_FEATURE
<222> LOCATION: (1)..(1)
<223> OTHER INFORMATION: Corresponds to Z (at least one amino acid-
      preferably Leu or Pro)

```
<220> FEATURE:
<221> NAME/KEY: MISC_FEATURE
<222> LOCATION: (2)..(2)
<223> OTHER INFORMATION: Corresponds to Y (any amino acid- preferably
      Asp or Ala)
<220> FEATURE:
<221> NAME/KEY: MISC_FEATURE
<222> LOCATION: (3)..(3)
<223> OTHER INFORMATION: Corresponds to X (any amino acid- preferably
      Pro)

<400> SEQUENCE: 17

Xaa Xaa Xaa Arg Gly Pro Arg Pro
1               5

<210> SEQ ID NO 18
<211> LENGTH: 8
<212> TYPE: PRT
<213> ORGANISM: Artificial Sequence
<220> FEATURE:
<223> OTHER INFORMATION: Peptide derivative

<400> SEQUENCE: 18

Leu Val Pro Arg Gly Pro Arg Pro
1               5

<210> SEQ ID NO 19
<211> LENGTH: 8
<212> TYPE: PRT
<213> ORGANISM: Artificial Sequence
<220> FEATURE:
<223> OTHER INFORMATION: Peptide derivative

<400> SEQUENCE: 19

Ala Asp Pro Arg Gly Pro Arg Pro
1               5

<210> SEQ ID NO 20
<211> LENGTH: 8
<212> TYPE: PRT
<213> ORGANISM: Artificial Sequence
<220> FEATURE:
<223> OTHER INFORMATION: Peptide derivative

<400> SEQUENCE: 20

Leu Asp Pro Arg Gly Pro Arg Pro
1               5

<210> SEQ ID NO 21
<211> LENGTH: 8
<212> TYPE: PRT
<213> ORGANISM: Artificial Sequence
<220> FEATURE:
<223> OTHER INFORMATION: Peptide derivative

<400> SEQUENCE: 21

Leu Val Pro Arg Gly Pro Arg Val
1               5

<210> SEQ ID NO 22
<211> LENGTH: 6
<212> TYPE: PRT
<213> ORGANISM: Artificial Sequence
<220> FEATURE:
<223> OTHER INFORMATION: Spacer sequence

<400> SEQUENCE: 22

Gly Gly Gly Gly Gly Gly
```

```
<210> SEQ ID NO 23
<211> LENGTH: 5
<212> TYPE: PRT
<213> ORGANISM: Artificial Sequence
<220> FEATURE:
<223> OTHER INFORMATION: Spacer sequence

<400> SEQUENCE: 23

Gly Gly Gly Gly Gly
1               5

<210> SEQ ID NO 24
<211> LENGTH: 11
<212> TYPE: PRT
<213> ORGANISM: Artificial Sequence
<220> FEATURE:
<223> OTHER INFORMATION: Peptide derivative

<400> SEQUENCE: 24

Gly Pro Arg Pro Gly Gly Gly Gly Gly Gly Cys
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Peptide derivative

<400> SEQUENCE: 25

Leu Val Pro Arg Gly Pro Arg Pro Gly Gly Gly Gly Gly Cys
1               5                   10                  15
```